US012714557B2

(12) United States Patent
Kiss et al.

(10) Patent No.: US 12,714,557 B2
(45) **Date of Patent: *Aug. 25, 2026**

(54) SELF-EXPANDABLE STENT AND SET OF STENTS

(71) Applicant: P+F Products + Features GmbH, Vienna (AT)

(72) Inventors: Katharina Kiss, Vienna (AT); Guilherme Agreli, Sao Paulo (BR)

(73) Assignee: P+F Products + Features GmbH, Vienna (AT)

(*) Notice: Subject to any disclaimer, the term of this patent is extended or adjusted under 35 U.S.C. 154(b) by 992 days.

This patent is subject to a terminal disclaimer.

(21) Appl. No.: 17/499,298

(22) Filed: Oct. 12, 2021

(65) Prior Publication Data

US 2022/0151775 A1 May 19, 2022

Related U.S. Application Data

(63) Continuation of application No. PCT/EP2020/082097, filed on Nov. 13, 2020.

(51) Int. Cl.
*A61F 2/24* (2006.01)

(52) U.S. Cl.
CPC .......... *A61F 2/2418* (2013.01); *A61F 2/2475* (2013.01); *A61F 2230/0071* (2013.01); *A61F 2240/001* (2013.01); *A61F 2250/0039* (2013.01); *A61F 2250/0064* (2013.01)

(58) Field of Classification Search
CPC .............. A61F 2/2475; A61F 2240/001; A61F 2/2463; A61F 2/2412; A61F 2/2415
See application file for complete search history.

(56) References Cited

U.S. PATENT DOCUMENTS

| | | | | |
|---|---|---|---|---|
| 11,406,100 | B2 * | 8/2022 | Zhong | A61P 9/00 |
| 2011/0301700 | A1 | 12/2011 | Fish et al. | |
| 2014/0128969 | A1 | 5/2014 | Hill et al. | |
| 2017/0165059 | A1 | 6/2017 | Roselli et al. | |
| 2019/0001023 | A1 * | 1/2019 | Ashworth | A61L 27/3687 |

(Continued)

FOREIGN PATENT DOCUMENTS

| | | | |
|---|---|---|---|
| CN | 102670333 | A | 9/2012 |
| CN | 102961199 | A | 3/2013 |
| CN | 106073945 | A | 11/2016 |

(Continued)

OTHER PUBLICATIONS

International Search Report and Written Opinion issued Nov. 29, 2021 in corresponding International Patent Application No. PCT/EP2020/082097, filed Nov. 13, 2020.

(Continued)

*Primary Examiner* — Bruce E Snow
(74) *Attorney, Agent, or Firm* — Spencer Fane, LLP

(57) ABSTRACT

A self-expandable stent has a dry valve made of bovine pericardium arranged at a proximal end thereof, a skirt surrounding the dry valve at the proximal end of the stent and made of one of bovine pericardium and polyester. The dry valve is configured to be rehydrated when placed in contact with a solution, and the stent includes eyelets arranged at the proximal end of the stent for fixing the stent at a point of interest, with the point of interest being one of the vena cava superior and the vena cava inferior.

20 Claims, 3 Drawing Sheets

(56) References Cited

U.S. PATENT DOCUMENTS

2021/0187135 A1* 6/2021 Claessens ............. A61F 2/0095

FOREIGN PATENT DOCUMENTS

| | | |
|---|---|---|
| CN | 206995366 U | 2/2018 |
| CN | 110279495 A | 9/2019 |
| EP | 3 184 082 A1 | 6/2017 |
| EP | 3 342 377 A1 | 7/2018 |
| EP | 3 693 030 A1 | 8/2020 |

OTHER PUBLICATIONS

Chinese Search Report issued Oct. 15, 2021 in corresponding Chinese Patent Application No. 202080003828 (published as CN113423363A), with English Translation.

* cited by examiner 10a
10b
PE
MP
DE
TA
12
14
16
18
20
22

50
40
36
30
32
38
42
48
B

SELF-EXPANDABLE STENT AND SET OF STENTS

CROSS-REFERENCE TO RELATED APPLICATION

This application is a continuation application of International Patent Application No. PCT/EP2020/082097, filed Nov. 13, 2020, the contents of which are hereby incorporated herein by reference in their entirety.

BACKGROUND

Field of the Invention

The present invention relates to a self-expandable stent having a dry valve. Furthermore, the invention relates to a set of stents comprising two self-expanding stents according to the invention and a delivery device for delivering a self-expandable stent according to the invention.

Background Information

A healthy heart function provides necessary blood flow to the body. The anatomy of the heart is comprised of four chambers: the right atrium, right ventricle, left atrium and left ventricle. There are valves located between the two right chambers (tricuspid valve) and the left chambers (mitral valve). Blood travels from the caval veins, the superior vena cava and inferior vena cava, to the right atrium. From the right atrium, blood passes through the tricuspid valve into the right ventricle. From there, blood flows through the pulmonary valve to the lungs. Following oxygenation, the blood flows back to the left atrium, through the mitral valve and into the left ventricle. Blood is then pushed through the aortic valve and from there, ultimately, to the rest of the body.

The tricuspid valve is located between the right atrium and ventricle, whereas the mitral valve is located between the left atrium and ventricle. The native valves consist of two and three leaflets respectively for the mitral and the tricuspid valve. The base of these leaflets is attached to the opening connecting both the atrium and the ventricle, creating a non-circular valve annulus. Chordae tendinae are attached to the caudal ends of the leaflets, connecting the leaflets to the myocardial wall via papillary muscles.

Proper opening and closing of the atrioventricular valves is dependent on the function of all of the structures involved with leaflet function, specifically the annulus, the leaflets, the chordae tendinae, the papillary muscles and a healthy myocardial wall. During ventricular filling (diastole), the atrioventricular valves remain open and during ventricular contraction (systole), the valves close as a consequence of complete leaflet apposition. In instances where complete apposition of the leaflets is not achieved, leakage or regurgitation across the valve affects cardiac performance and health. Severe regurgitation or leakage can lead to hemodynamic deterioration and/or heart failure.

SUMMARY

It has been found that moderate or higher tricuspid valve regurgitation affects cardiac functional performance, and is typically indicative of a broader primary disease such as left heart dysfunction. Primary dysfunction can include pulmonary hypertension, right ventricular volume overload and right ventricular disease. Similarly, mitral regurgitation or leakage is primarily due to degenerative valve disease. The presence of dysfunctional support structures also contributes to mitral regurgitation, specifically as a consequence of a heart attack (ischemic mitral regurgitation) or ventricular dilation (functional mitral regurgitation). Other causes of atrioventricular regurgitation include acquired conditions (i.e. endocarditis, rheumatic heart disease) and congenital anomalies.

Atrioventricular regurgitation also impacts the caval veins leading to the atrium. During tricuspid regurgitation, pressure and flow changes in the right atrium causes the inferior vena cava (IVC) and the superior vena cava (SVC) to dilate. Additionally, veins feeding the IVC and the SVC are also impacted by these effects. Specifically, tricuspid regurgitation causes the azygos and the hepatic veins, which are located cranial and caudal to the right atrial opening respectively, to dilate. This leads to overall hemodynamic deterioration and liver dysfunction. Physical symptoms of tricuspid regurgitation include fatigue, loss of appetite and abdominal fullness. Similarly, mitral regurgitation impacts the pulmonary vein and can cause fluid buildup in the lungs. Chronic mitral regurgitation often leads to left ventricular remodeling or dilation of the left ventricle. Physical symptoms of mitral regurgitation include fatigue, decreased exercise tolerance, shortness of breath, and swollen feet. If left untreated, either atrioventricular severe regurgitation can lead to pulmonary hypertension, atrial fibrillation or heart failure.

Biological tissues are widely used to make prosthetic replacements for heart valves and blood vessels as well as for transcatheter heart valves. They are connective tissues comprising collagen as the main component. Among these tissues, bovine pericardium is one of the most widely employed. Pericardial tissue is the sac surrounding the heart which provides a natural barrier to infection for the heart and prevents adhesion to the surrounding tissue. The pericardium also serves mechanical roles, for example, by preventing over dilation of the heart, maintaining the correct anatomical position of the heart, and regulating the pressure to volume ratio in the left ventricle during diastole. The structure of the tissue determines its behavior under loading in both conditions physiologic to the pericardium and as a prosthetic device.

However, biological tissues obtained from the abattoir, in particular porcine and bovine cadavers, begin to degrade immediately. Therefore, the storage of such materials has proven to be difficult. For this purpose, a biological tissue, such as e.g. bovine or porcine pericardium or a heart valve, is usually chemically treated to improve its mechanical performance and immunogenic properties, reduce thrombogenicity and degradation, preserve sterility, and prolong the allowable storage period.

Accordingly, biological tissues are known which can be used as bioprosthetic devices that can be stored dry before used for clinical applications. Additionally, special care has to be taken in connection with the preparation methods in order to avoid the formation of degenerative calcific deposits. Calcification, in particular pathologic calcification, of soft biological tissues due to deposition of calcium phosphate mineral salts in an implanted tissue is undesirable and the deposition of the calcific deposits can have severe consequences on device performance. Calcification of implants can lead to stiffening, structural instability and ultimately to device failure.

Although there are difficulties in the usage of biological tissues, their performance inside a human body has proven to be significantly better.

It is therefore an object of embodiments of the invention to provide a self-expandable stent having a dry valve, a set of stents comprising two self-expandable stents having a dry valve and a delivery device for delivering a self-expandable stent with which the above mentioned drawbacks can be overcome. This object is solved by the subject matter disclosed herein.

In particular, in a first aspect the invention relates to a self-expandable stent having a dry valve made of bovine pericardium arranged at a proximal end thereof, a skirt surrounding the dry valve at the proximal end of the stent and made of one of bovine pericardium and polyester, wherein the dry valve is configured to be rehydrated when placed in contact with a solution, and the stent comprising eyelets arranged at the proximal end of the stent for fixing the stent at a point of interest, with the point of interest comprising one of the vena cava superior and the vena cava inferior.

Thus, the present disclosure relates to embodiments of the invention of a medical device for a minimally invasive preferably heterotopic treatment of tricuspid valve leakage or regurgitation and other similar cardiac conditions. Heterotopic placement indicates that the prosthesis will not be implanted directly at the annulus of the tricuspid valve. To treat tricuspid valve regurgitation, implants should be placed at the atrial junction of the Superior Vena Cava (SVC) and/or of the Inferior Vena Cava (IVC)—termed caval veins.

Due to the possible placement of such a stent comprising a dry valve at a heterotopic location, it is reasonable to expect that the presence of valves at the atriocaval junction may impact backflow into the veins. Impacting the backflow into the veins can cause an increase in the pressure inside the right atrium and thus limit regurgitation across the tricuspid valve thereby enhancing the function of the heart once such a surgical valve has been deployed.

In this connection it is noted that the expressions “proximal” and “distal” relate to the position of the stent in use, i.e. to positions closer to and further away from the heart. The vena cava superior (SVC) relates to the vein, which is connected to the upper part of the right atrium of the heart whereas the vena cava inferior (IVC) is generally connected to the lower part.

Embodiments of the invention provide a stent, which can be fixed at a point of interest such as in one of the caval veins in order to treat one of above mentioned diseases. In order to seal the fixing point, the stent further comprises a skirt, which is arranged at a proximal end of the stent, i.e. at the part of the stent which in use is arranged closer to the heart. The skirt therefore also provides sealing between the stent and the right atrium of the heart.

The stent further comprises a dry valve made of bovine pericardium, which upon final placement at the point of interest can be rehydrated with a solution such as a saline solution. Hence, a pericardium as an animal biological tissue material is used, in particular obtained from a bovine heart that may have been treated with a crosslinking agent. The natural human heart valve, which is supposed to be fixed with the invention, is identified as the tricuspid valve. Therefore, the pericardium tissue is used to replace the damaged or diseased naturally occurring heart valve. Also, such a valve can allow the pre-loading of the stent within a delivery system.

The valves are thus made using bovine pericardium. The ECM (Extracellular Matrix) tissue is generally harvested from the pericardial sac of cows and is then used to manufacture the leaflets. The tissue from the pericardial sac is particularly well suited for a valve leaflet due to its durable physical properties. The tissues are glutaraldehyde fixed, non-viable, chemically treated (decellularized) and sterilized so that the biological markers are removed making them more compatible with the patient’s immune system.

Preferably, there are three leaflets used for each type of valve included in the stent that can be fixed to the IVC or to the SVC. This enables the regurgitation to be reduced.

The potential benefits of bovine pericardium are superior biocompatibility, demonstrates minimal suture line bleeding and patency can be immediately confirmed by TEE ultrasound. They also have benefits like lack of calcification, support of cellular ingrowth and reduced rates of restenosis and infection. The pericardium is durable, strong and available in various sizes.

The skirt surrounding the dry valve at the proximal end of the stent is also made of one of bovine pericardium and polyester to provide a stent with a good performance.

To assist the fixation of the valve to the heart the valve can have a PET fabric skirt that attaches the tissue to the stent frame. PET material is highly inert and does not create any adverse reaction in human body. The PET material also permits ingrowth of cells into the cloth which helps hold the valve in place minimizing thrombosis at the same time.

The superior vena cava valve can have a comparatively long skirt which helps in preventing PVL—Para Valvular Leaks after implantation. In case of an inferior vena cava valve, the skirt is comparatively short which helps in prevention of hepatic vein occlusion.

Generally speaking PTFE suture line can be used for fixation on fixing the stent to the heart.

The stent can be reliably used to treat patients suffering from acute type A dissection, ascending aorta aneurysm, or other conditions that require urgent intervention.

By way of such a stent according to embodiments of the invention the time of treatment of a patient can be significantly reduced leading to reduced mortality rates for acute aortic syndromes, provided the patient is within the vicinity of a medical facility. This is because the valve replacement device in the form of the stent according to embodiments of the invention can save time to treatment when this is transported to the heart via a arterial femoral access. This is particularly the case if the valve is pre-loaded at a delivery device and the equipment is ready to use from a shelf According to a first embodiment of the invention the stent comprises a distal end and a middle part arranged between the proximal end and the distal end. The middle part is further spaced approximately 20 to 40% from the distal end and approximately 20 to 40% from the proximal end, i.e. extends over approximately 20 to 60% of a length of the stent. Hence, it can be seen that the stent can be divided in three parts. Such lengths, sizes and dimensions of the respective parts are believed to be particularly suitable for a minimally invasive treatment of acute type A dissection, ascending aorta aneurysm, or other conditions that require urgent intervention. Selecting the length of the middle part to be longer than that of the proximal end enables an interference fit between the stent and either one of the SVC and the IVC to be sufficient to prevent the stent from becoming dislodged in time. The outwardly directed arms can advantageously be configured to act like barbs or hooks in the expanded state of the stent in order to ensure that the dry valve remains at its intended location, the location at which it was deployed.

According to a second embodiment the stent comprises a frame composed of a plurality of arms forming the three interconnected parts, i.e. the proximal end, the distal end and the middle part. The expansion of the stent is made possible by the plurality of arms that are interconnected in such a way that following the expansion they adapt to the anatomical need of the location of the stent. In this way the design of such a stent is adapted to accommodate the anatomical needs and implantation locations. The stent furthermore consists of a self-expandable stent frame. Moreover, between 6 and 50 arms can be provided to form the stent frame.

According to another embodiment, in the expanded state, the plurality of arms is outwardly directed at the distal end of the frame. These arms can then be used to additionally fix the stent to the SVC or the IVC as the case may be. They can furthermore comprise eyelets to allow suturing the distal end of the stent to the SVC or IVC.

According to another embodiment of the invention the frame is composed of Nitinol. Nitinol is a collapsible and flexible metal, which is furthermore self-expandable and comprises a shape-memory. Hence, the frame can automatically self-expand to an outer shape, which can be chosen beforehand since the Nitinol can memorize the chosen shape.

The stent can further comprise a device or means for attaching the proximal end of the stent at the vena cava or at the transition between the vena cava and the right atrium of a heart such that it can be ensured that the stent remains at its intended place.

The dry bovine pericardium can have a maximum tensile stress selected in the range of 15 to 25 MPa, and/or wherein the rehydrated bovine pericardium has a tensile stress selected in the range of 15 to 20 MPa. Thus, the dry bovine pericardium can comprise a tensile resistance which can be up to 15 times higher than the tensile resistance of the leaflets of a human heart. This is mainly done for safety reasons in order to minimize tearing or fracture of the pericardium.

The mechanical properties of a material, in particular tensile strength, can be tested under strain-stress evaluation using Universal Testing Machine (Oswaldo Filizzola, model AME-2kN).

According to another embodiment of the invention the dry bovine pericardium has a calcium content selected in the range of 0.01 g/Kg and 0.1 g/Kg, preferably in the range of 0.015 to 0.9 g/Kg, especially in the range of 0.02 to 0.05 g/Kg.

The bovine leaflets can generally be as flexible and durable similar to the patient's natural tissue and therefor individual with such replacement valve may not require blood thinner medication on a continuous basis. Bovine pericardium tissue provide better hemodynamics in view of their similarity to natural flexible leaflet valves, some bovine pericardium valves may have some limitation on durability due to calcification and degeneration process. Treating the valves with a specialized anti-calcification treatment makes them more resistant to calcification. The valves having such a calcium content are hence more resistant to calcification and are more durable.

The dry valve can comprise between two and six leaflets, preferably three or four leaflets. It has shown that for stents shaped circularly in the region of attachment of the valve, a valve comprising three leaflets is the best option in order to distribute the forces of the blood flow present in the heart evenly during the opening and closing process of the valve.

According to an embodiment of the invention the dry bovine pericardium is formed by treating using a method comprising the following steps: soaking of the dry bovine pericardium treated with a crosslinking agent with a saline solution; contacting the soaked bovine pericardium with an aqueous solution comprising Hydrogen Peroxide; contacting the bovine pericardium with an aqueous solution comprising PBS and EDTA; contacting the bovine pericardium with a solution comprising glycerol, ethanol and EDTA; and contacting the bovine pericardium with a glycerol solution.

One embodiment of the present invention utilizes soaking of the bovine pericardium treated with a crosslinking agent with a saline solution.

As used herein, a crosslinking agent is glutaraldehyde which is preferably used in biochemical and medicine applications as an amine-reactive homobifunctional cross-linker. As already mentioned above, glutaraldehyde treatment produces stable cross-links in cellular and extra-cellular matrix proteins which substantially reduced graft immunogenicity. However, such tissue has altered mechanical property, early mechanical failure, cytotoxicity, and incomplete suppression of immunological recognition. Besides this severe calcification was noticed in glutaraldehyde-treated bovine pericardium. An emerging alternative to glutaraldehyde treatment is further treatment according to the method steps, i.e. a method allowing to reduce calcification of the bovine pericardium.

It is preferably to use the crosslinking agent in an amount of from 0.1% to 5.0% by volume, more preferably from 0.2% to 3.0% by volume, further preferably from 0.3% to 2.0% by volume and especially preferably from 0.5% to 1.0% by volume.

In this respect, as a first step a soaking of the bovine pericardium with an aqueous saline solution comprising 0.9% of sodium chloride (9.0 g per litre) is carried out. Such a solution is also commonly named as normal saline, physiological saline or isotonic saline solution.

In a second step, the soaked bovine pericardium is contacted with an aqueous solution comprising Hydrogen Peroxide. It is preferred that the concentration of hydrogen peroxide is from 0.05% by volume to 5.0% by volume, preferably from 0.1% by volume to 3.0% by volume, more preferably from 0.2% by volume to 2.0% by volume.

In a third step of the present invention, the bovine pericardium is contacted with an aqueous solution comprising PBS and EDTA.

As used herein, the term "contacting" means treating, immersion, exposing to, rinsing of the biological tissue used in the inventive method.

As used herein, the term "PBS" is directed to a phosphate buffered saline having a pH of 7.4 and containing water based salt solution of disodium hydrogen phosphate, sodium chloride and, in some formulations, potassium chloride and potassium dihydrogen phosphate. PBS is used in biological and medical applications, such as washing cells, transportation of tissues and dilutions, because PBS closely mimics the pH, osmolarity, and ion concentrations of the human body.

The term "aqueous solution" refers to a solution comprising a substance or a compound and water that has been purified to remove contaminants which are able to influence the end product. Preferably, distilled water, double distilled water or deionized water is used in an embodiment of a method of the present invention.

The term "EDTA" is used herein to refer to ethylenediaminetetraacetic acid which is a complexing chelating agent being able to sequester metal ions especially like $Fe^{2+}/Fe^{3+}$, $Al^{3+}$, $Mg^{2+}$, $Ca^{2+}$, $Mn^{2+}$, $Zn^{2+}$ and others and to remove them from the solution forming so called EDTA-complexes.

According to an embodiment, it is especially important to remove calcium ions from the solution by forming calcium chelator that has been shown to inhibit mineralization of biological tissues, in particular bovine pericardium tissue. It is suggested that EDTA binds to calcium ions on the outer shell of hydroxyapatite crystals which are formed from calcium phosphate crystals thereby chelating and removing calcium ions from the crystals, causing the tissue material to shrink thus demineralizing the material.

Treatment of biological tissues with EDTA hence slows down the progression of calcification by binding calcium before it can react to form hydroxyapatite. Since the calcification of biological tissues used e.g. as bioprosthetic heart valves is a clinically significant problem that contributes to implant failure, it is of significant importance to reduce calcium level in biological tissues used as an implant. Therefore in an embodiment of the present invention, the EDTA treatment can reduce calcium level in biological tissues, especially in bovine or porcine pericardium or a heart valve preferably by 20%, more preferably by 30%, further preferably by 40% and especially preferably by 50%. Further, it is preferable to use EDTA in combination with PBS in order to increase demineralization and compatibility with a human body.

Furthermore, it is preferable to use EDTA, in particular in steps (3) and (4), having a concentration of more than 0.01% by weight, preferably of more than 0.05% by weight, more preferably of more than 0.10% by weight, still preferably of more than 0.15% by weight, and of less than 10.0% by weight, preferably of less than 8.0% by weight, more preferably of less than 6.0% by weight, still preferably of less than 5.0% by weight, further preferably of less than 3.0% by weight. Still further in the present invention, it is preferably to use disodium EDTA.

In a fourth step of the present invention, the bovine pericardium is contacted with a solution comprising glycerol, ethanol and EDTA, and in a fifth step the bovine pericardium is contacted with a glycerol solution in order to further reduce calcification of biological tissue and to dehydrate the bovine pericardium. The following steps describe an implementation of these processes in the method.

After the bovine pericardium has been processed through steps (1) to (3) of the method, they undergo the treatment in a solution comprising glycerol, ethanol and EDTA.

Phospholipids in and around biological tissue cells have been found the most prominent calcification nucleation sites. Therefore, the removal of these tissue components has been proposed to reduce mineralization, in particular calcification. Different studies have shown these to be effective calcification prevention strategies. The organic solvents like ethanol or glycerol or a mixture of ethanol and glycerol can be similarly used for this purpose. For example, the treatment with at least 70% ethanol, preferably with at least 80% ethanol, more preferably with at least 90% ethanol, extracts phospholipids from the tissue while also causing a change in collagen conformation that increases bioprosthesis resistance to collagenase. Thus, ethanol treatment allows extracting almost all phospholipids and cholesterols from the bioprosthesis, thus eliminating calcification of the biological tissue cells. Additionally, ethanol treatment also prevents adsorption of phospholipids and cholesterols from the solution. The method by which glycerol fixes biological tissue is not jet fully understood, but a 98% concentration, preferably 99% concentration, is sufficient to treat the biological tissue to make the tissue more biocompatible and resistant to calcification.

In this respect, it is preferably to treat biological tissue in a solution comprising glycerol, ethanol and EDTA for at least 60 minutes, preferably for at least 75 minutes, more preferably for at least 90 minutes, at room temperature, in particular at a temperature of 10° C. to 25° C., preferably at a temperature of 15° C. to 25° C., more preferably at a temperature of 18° C. to 22° C., under stirring of not more than 500 rpm, preferably of not more than 300 rpm, more preferably of not more than 50 rpm. During this time most of the water molecules presented in biological tissue, in particular pericardial tissue, are replaced with glycerol.

Furthermore, it is preferable to use a mixture of glycerol and ethanol, wherein a volume ratio of glycerol to ethanol is preferably from 1:5 to 5:1, more preferably from 1:4 to 4:1, still preferably from 1:3 to 3:1, further preferably from 1:2 to 2:1.

The bovine pericardium is then removed from the solution and placed in glycerol for further dehydration for at least 60 minutes, preferably for at least 75 minutes, more preferably for at least 90 minutes, at room temperature, in particular at a temperature of 10° C. to 25° C., preferably at a temperature of 15° C. to 25° C., more preferably at a temperature of 18° C. to 22° C., under stirring of not more than 500 rpm, preferably of not more than 300 rpm, more preferably of not more than 50 rpm.

It can further be preferable to use an additional step of contacting or rinsing the bovine pericardium with ethanol having a concentration of at least 70% by volume, preferably with at least 80% by volume, more preferably with at least 90% by volume. The additional step, in particular step (3a), is preferably carried out before contacting the biological tissue with a solution comprising glycerol, ethanol and EDTA. It can further be preferable to carry out another additional step (5a) of contacting the biological tissue with ethanol after the step of contacting the biological tissue with a glycerol and before the step of drying the biological tissue. It can still further be preferable to carry out an additional step (3a) and/or (5a) using a mixture of ethanol and EDTA having a concentration as in step (3) or (4).

The bovine pericardium is removed from the solution and exposed to ambient air or an inert environment, e.g. nitrogen, at room temperature and humidity so as not to adversely affect tissue properties. Preferably, the drying is performed in a clean room at ambient conditions for at least 12 hours, preferably for at least 16 hours, still preferably for at least 20 hours. Further preferably, the drying is performed under high efficiency particulate air (HEPA) filter, in particular under HEPA conditions in a clean room. As used herein, the term "ambient conditions" is directed to the ambient temperature of more than 10° C., preferably of more than 12° C., more preferably of more than 14° C., especially preferably of more than 18° C., and preferably of less than 25° C., more preferably of less than 23° C., further preferably of less than 22° C. Further an embodiment of the present invention it is preferably to carry out each of steps (1) to (7) at the ambient conditions as described above.

The treated and dried bovine pericardium is then packaged in a container or package essentially free of liquid for subsequent surgical implantation. As used herein, the term "essentially free of liquid" means a non-fluid environment in which the presence of water or other substances is limited to approximately the content of such substances in ambient air.

According to another embodiment the stent is configured to be placed in the vena cava superior.

In the expanded state, a maximum outer diameter of the middle part can be larger than a maximum outer diameter of the proximal end. Such a design has proven to fit best in the SVC.

A transition between the middle part and the distal end can have an outer diameter that is less than the maximum outer diameter of the middle part and less than an outer diameter of the distal end in the expanded state. By forming the stent in this way an attachment of the stent at the vena cava superior's root can be improved.

According to an embodiment the skirt surrounds at least the proximal end and parts of the middle part of the stent, preferably up to ¾ of a length of the middle part to ensure a good sealing behavior between the SVC and the right atrium of the heart.

In the expanded state, the maximum outer diameter of the distal end and a maximum outer diameter of the proximal end can generally be the same, i.e. a difference between the maximum outer diameter of the distal end and the maximum outer diameter of the proximal end lies in the range of 0 to 10%. Such a design can help to improve the interference fit of the stent inside the SVC.

According to another embodiment all of the ends of the arms at the distal end lie in a common plane and can comprise eyelets. Such eyelets can help to suture the stent frame to the SVC.

According to a different embodiment of the invention the stent is configured to be placed in the vena cava inferior.

In the expanded state, a maximum out the diameter of the stent can generally increase from the proximal end to the distal end. Such diameters have been found to be required for accurate placement at the aortic valve and the aortic root The skirt can surround at least the proximal end of the stent, preferably up to ¼ of a length of the stent to provide a seal between the IVC and the right atrium of the heart.

Furthermore, all of the ends of the arms at the distal end lie in a common plane and can comprise eyelets. As already mentioned above in connection with the SVC, such eyelets can also help to suture the stent frame to the IVC.

According to another aspect of the invention a set of stents comprising two self-expendable stents is provided, both stents having a dry valve made of bovine pericardium arranged at a proximal end thereof, a skirt surrounding the dry valve at the proximal end of the stent and made of one of bovine pericardium and polyester, wherein the dry valve is configured to be rehydrated when placed in contact with a solution, and eyelets arranged at the proximal end of the stent for fixing the stent at a point of interest such as the vena cava superior or inferior. A first stent is configured to be placed in the vena cava superior and a second stent is configured to be placed in the vena cava inferior. In order to avoid regurgitation in one of the caval veins usually two stents are implanted, one at the SVC and one at the IVC, respectively. In this connection the respective stents can comprise the features which have been described above, where one stent is configured to be placed in the SVC whereas a second stent is configured to be placed in the IVC.

A device for delivering a self-expandable stent according to the invention, the delivery device comprising a flush port, a main body part for holding, inflating and/or releasing the stent and an actuation mechanism for moving the stent to a delivery site.

The device can be preloaded with a stent so that this can be stored ready to use on a shelf in a medical facility to significantly reduce the treatment time of acute aortic syndromes leading to reduced mortality rates of acute aortic syndromes.

The actuation mechanism can have a torque control and may be able to rotate the stent about an axis of the main body. In this way the stent can be positioned in relation to the extremities in an as good as possible manner at the aortic valve, to deploy the valve and stent at the desired deliver site.

The device can be improved with steerable control, to increase precision and accuracy at deployment.

The device can have a knob or the like at the actuation mechanism, with the knob in particular being able to be rotated about an axis of rotation of the actuation mechanism. By turning the knob the lumen is able to deflect and allows a better positioning of the tip and the main body of the delivery device and less stress over the system during deployment. This leads to an improved accuracy of deployment of the delivery device and hence of a stent that is delivered to a delivery site using the delivery device.

BRIEF DESCRIPTION OF THE DRAWINGS

The invention will be explained in more detail hereinafter with reference to the drawings.

FIG. 1A and FIG. 1B both show self-expandable stents 10 in different sizes. The stents 10*a* of FIG. 1A relate to stents, which are configured to be placed in the SVC whereas the stents 10*b* of FIG. 1B relate to stents configured to be placed in the IVC.

DETAILED DESCRIPTION

All embodiments of the stents according to the invention comprise a frame 12 made out of a plurality of arms 14 which are fabricated of Nitinol. Nitinol is a flexible metal, which comprises the characteristic of being self-expendable. Hence, the stents 10 can be delivered in a compressed state to a point of interest such as the SVC or the IVC of a human since they can self-expand once they are deployed.

Figures 1A, 1B:
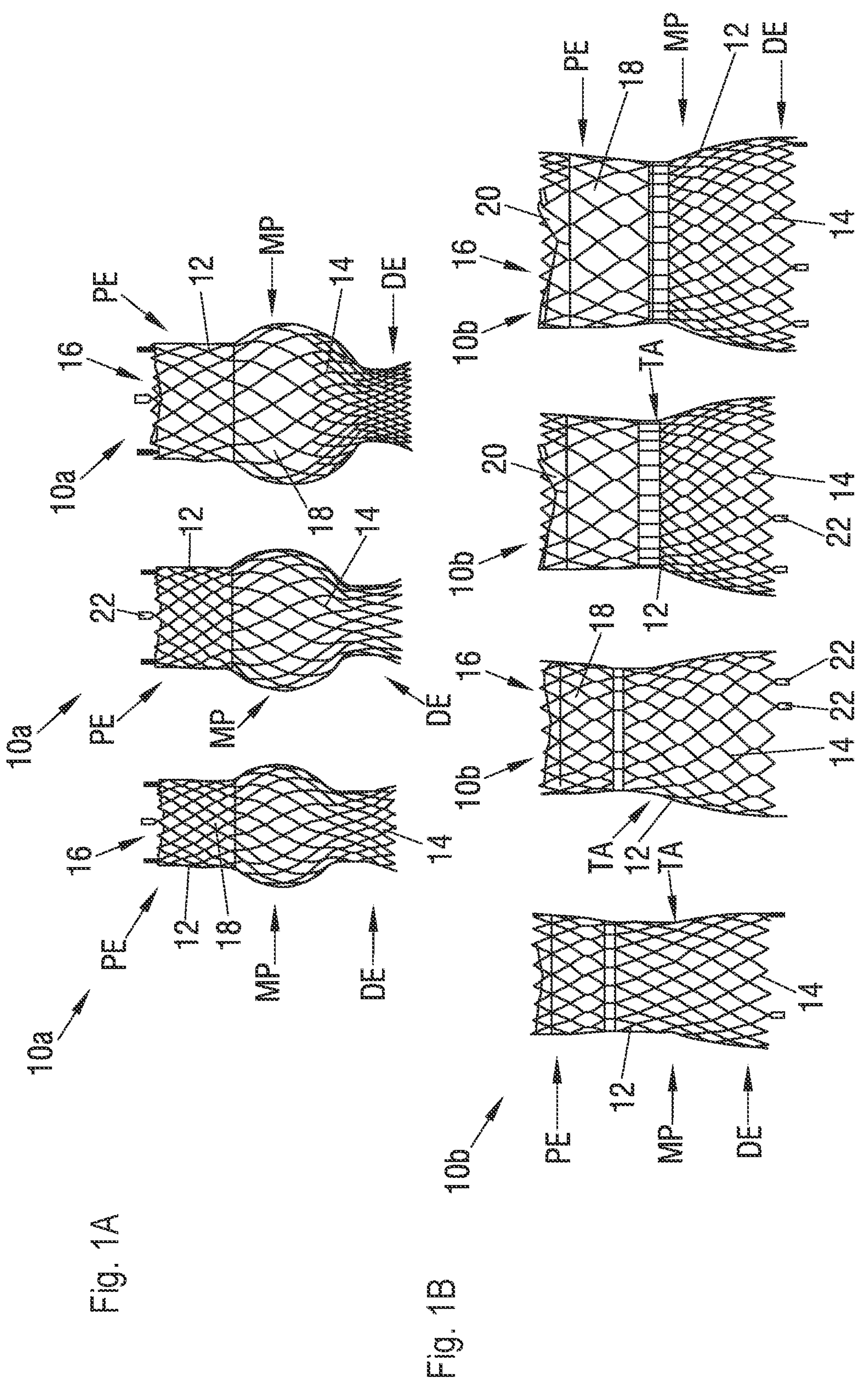
FIG. 1A and FIG. 1B are examples of stents according to the invention in different sizes.

The frames 12 further comprise three parts, i.e. a proximal end PE, a distal end DE and a middle part MP, which are interconnected by the arms 14. The proximal end PE is characterized by being the end of the stent 10 which further includes a valve 16 made out of dry bovine pericardium as well as a skirt 18 made out of dry bovine pericardium and polyester. FIG. 1B also shows the leaflets 20 of the valve 16. The valve 16 can comprise between 2 and 6, preferably 4, leaflets.

Figure 2:
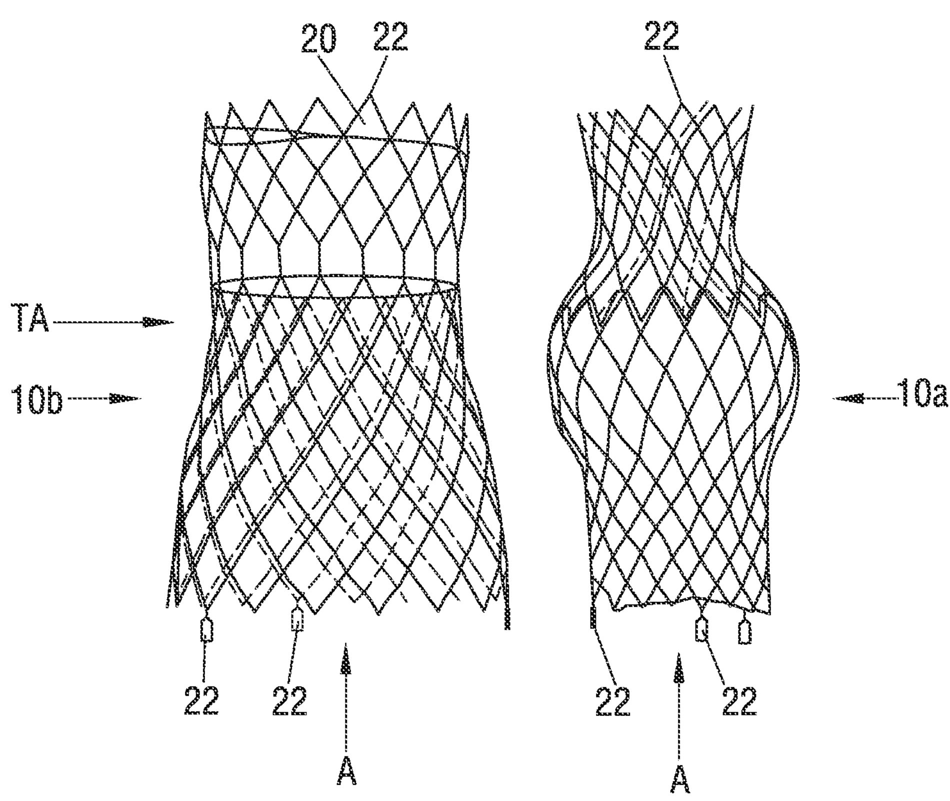
FIG. 2 is a photograph of a set of stents according to the invention.

In order to be able to attach the stents 10 at their respective points of interests, they comprise eyelets 22 at least at their respective proximal end PE, preferably at both ends PE and DE (see e. g. FIG. 2). That is, after being expanded, the stents 10 do not only hold themselves in place by fitting into their assigned vein but also be being sutured. This way, it may also be possible to attach the proximal end PE of a stent 10 at the transition between the SVC or IVC and the right atrium of a heart or at the wall of the right atrium itself The exact attachment point and technique can thus be chosen according to the different conditions at the different hearts which are being treated.

As one can see in FIGS. 1A, 1B and 2 the stents 10*a* and 10*b* can comprise different shapes in the expanded state. The reason for this lies in the fact that the different veins, namely the SVC and IVC, in which the stents 10 are supposed to be delivered, comprise different anatomies and/or conditions. Therefore, the shapes of the stents 10*a* and 10*b* are designed such that they fit best into their assigned vein.

Stent 10*a* of FIG. 1A, for example, is designed such that it fits in the vena cava superior SVC. It has shown that with a stent 10 shaped such that, in the expanded stat, the diameter of its middle part MP is bigger than the diameters of the proximal and distal ends PE, DE the best results can be achieved. One can also see that at a transition point between the middle part MP and the distal end DE the diameter of the stent decreases before increasing again. Furthermore, at the distal end DE the arms 14 are shaped such that they diverge, i.e. they point outwardly, to provide a good fitting behavior.

Additionally, due to anatomical reasons of the SVC, the skirt 18 of stent 10*a* does not only surround the proximal end PE of the stent 10*a* but also most of the middle part MP, i.e. up to ¾ of a length of the middle part, as well to prevent leakage between the stent 10*a* and the right atrium of the patient's heart.

Thus, the outer shape of the stent 10*a* can be described as follows: Starting at the proximal end PE of the stent 10*a* one can see that said end comprises eyelets 22, which have a rectangular outer shape with a rectangular opening therein, through which a thread for suturing the stent 10*a* to the SVC can be guided.

The proximal end PE comprises an essentially cylindrical shape, wherein the arms 14 of the frame 12 are connected such that they form a net with diamond-shaped openings. The middle part MP of the stent 10*a* is directly connected to the proximal end PE and comprises an essentially spherical outer shape. Thus, the diamond-shaped openings of the net formed by the arms 14 are bigger compared to the ones present at the proximal end PE.

At the other end of the middle part MP the stent 10*a* comprises its distal end DE, which again comprises a diameter that is smaller than the diameter of the middle part MP. Obviously, the diamond-shaped openings thus comprise an area which is smaller compared to the openings of the middle part MP.

The smaller the diameter of the distal end DE is, the smaller also the area of the openings is. At the very end of the distal end DE the arms 14 are faced outwardly in order to ensure a good interference fit of the stent 10*a* at the SVC.

The diameter of the distal end DE of the stent can be almost the same as the diameter of the proximal end PE of the stent 10*a* or can be significantly smaller (see FIG. 1A from left to right). Hence, the outer shape of the frame 12 of the stent 10*a* could be described as balloon-like. The ends of the arms 14 at both ends PE, DE of the stent 10*a* all lie in one plane.

In some embodiments also the distal end DE of the stent 10*a* can comprise eyelets 22 which can be formed in the same way as the eyelets of the proximal end PE. It is also possible that said distal eyelets comprise a different shape, e. g. a circular shape. The eyelets 22 extend from the plane in which the ends of the arms 14 lie.

A corresponding stent 10 for the placement inside the IVC is shown in FIG. 1B. It can be seen that the frame 12 of stent 10*b,* in the expanded state, is shaped such that the diameter of the stent generally increases from the proximal PE to the distal end DE of the stent 10*b*. At the middle part MP the stent 10*b* comprises a transition area TA where the diameter of the stent 10*b* increases significantly. It can be seen from FIG. 1B that the difference in diameter increase is even more significant the bigger the diameter in general is.

The skirt 18 of stent 10*b* only covers the proximal end PE of the stent 10*b* as well as small part of the middle part MP. As one can obviously see, the skirt 18 of stent 10*b* is significantly shorter than the one of stent 10*a*. This difference again arises due to the anatomical differences of the SCV and the IVC.

Thus, the outer shape of the stent 10*b* can be described as follows: Starting at the proximal end PE of the stent 10*a* can comprise eyelets 22, which can have a rectangular outer shape with a rectangular opening therein, through which a thread for suturing the stent 10*a* to the IVC can be guided. Said eyelets can also comprise another shape, i.e. for example a circular shape.

Furthermore, the proximal end PE comprises an essentially cylindrical shape, wherein the arms 14 of the frame 12 are connected such that they form a net with diamond-shaped openings.

Following the proximal end the stent 10*b* comprises a transition area TA at the middle part MP, where the arms 14 do not form diamond-shaped openings. Instead, the arms 14 are formed such that they are all parallel to each other. Said transition area can in some cases start precisely where the skirt 18 of the stent 10*b* terminates. In some embodiments the transition area TA can also be further away in a distal direction from said skirt 18. Nevertheless, the middle part MP of the stent 10*a* is directly connected to the proximal end PE.

The transition area TA extends over 5 to 20%, preferably over 8 to 15%, of the total length of the stent 10*b,* i.e. the region of parallel shaped arms 14 extends over 10 to 20% of the total length of the stent 10*b,* with the arms 14 extending in parallel to an axis A of the frame 12 (see FIG. 2). The axis A extends between the proximal and the distal end PE, DE of the frame 12 of the stent 10*b*.

At the transition area TA one can additionally see that the diameter of the middle part MP (and distal end DE) increases significantly compared to the diameter of the proximal end PE. Looking at FIG. 1B it can also be seen that the increase in diameter is even more significant the bigger the diameter is in the first place.

Also, following the transition area TA the arms 14 are again arranged netlike forming diamond-shaped openings. The area of said openings can be similar or smaller at the middle part MP and the distal end DE of the stent 10*b* compared to the area of the openings at the proximal end of the stent 10*b* (see FIG. 1B from left to right).

At the other end of the middle part MP the stent 10*b* comprises its distal end DE. The diameter of the stent 10*b* increases from the transition area TA to the distal end DE continuously. At the very end of the distal end DE the arms 14 are faced either straight downward (in a distal direction) or slightly outwardly in order to ensure a good interference fit of the stent 10*b* at the IVC. The ends of the arms 14 at both ends PE, DE of the stent 10*b* lie all in one plane.

In the embodiments shown in Fig, 1B also the distal end DE of the stent 10*b* comprises eyelets 22 having a rectangular outer shape with a rectangular opening for suturing the stent 10*b* to the IVC. Generally, the eyelets could also comprise a different shape, e. g. a circular shape. The eyelets 22 extend from the plane in which the ends of the arms 14 lie in.

Figure 3:
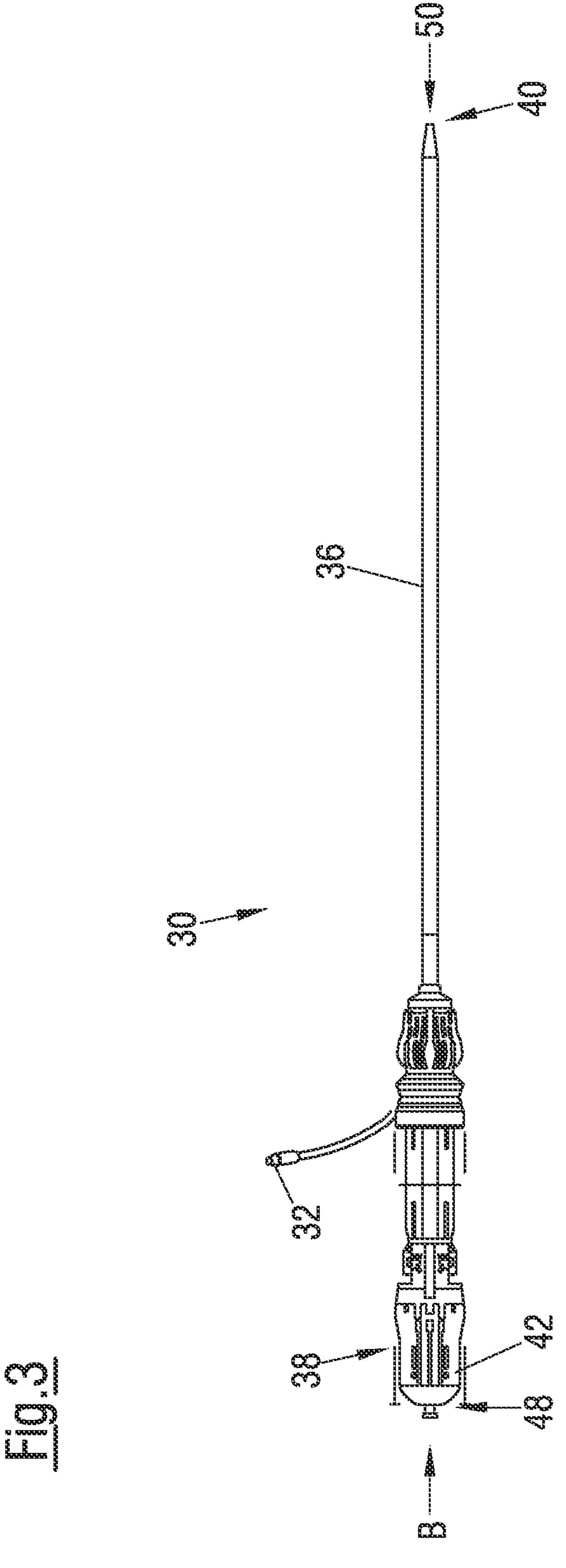
FIG. 3 is a device for delivering a self-expandable stent.

FIG. 3 shows a delivery device 30 for the self-expandable stent 10 also known as a catheter. The delivery device 30 comprises a flush port 32 for flushing internal cavities of the delivery device (not shown) and a main body 34 for holding, inflating and/or releasing the stent 10. The device can further comprise two valved introducers (not shown) to allow access to the stent 10. Initially two diagnostic catheters (not shown) can be introduced via said two valved introducers together with the preloaded stent for delivering the stent to the target delivery site, i.e. the patients' heart.

The device further includes an actuation mechanism 38 for moving the stent 10 to a delivery site.

The main body 34 is arranged at an inner shaft at an end of the lumen 36 that extends between the actuation mechanism 38 and a tip 40 of the catheter 30. The stent 10 can thus be guided to the delivery site by the actuation mechanism 38 that has a torque control and can rotate the stent 10 about an axis A of the frame 12. The axis A extends between the proximal and the distal end PE, DE of the frame 12 of the stent 10.

The actuation mechanism 38 comprises a knob 42 at a distal end 48 of the actuation mechanism 38. On turning the knob 48 about an axis B of the actuation mechanism 38 which extends between the distal end 48 and a proximal end 50 of the actuation mechanism 38, the lumen 36 is able to deflect. This enables the tip 40 of the lumen 36 to occupy various positions (not shown). Such a deflection of the lumen 36 reduces the overall stress in the system which leads to a better positioning of the stent 10 at a delivery site and an overall improved accuracy of deployment of the delivery device 30 and hence of a stent 10 that is delivered to a delivery site using the delivery device 30.

On delivering the stent 10 to the delivery site, i.e. the heart, by the delivery device 30, the arterial femoral access is preferably used. The lumen 36 is then moved through the arteries to the heart.

The position of the stent 10, the diagnostic catheters and/or of the delivery device 30 can be tracked using e.g. x-rays in order to monitor radiopaque markings present at the stent 10 and/or the delivery device 30. Thereby the precision and accuracy during deployment of the stent 10 within the heart can be further increased, so that the replacement valve 16 can be positioned accurately at the aortic valve.

The invention is further defined by the following embodiments:

The invention relates to a self-expandable stent according to a first embodiment having a dry valve (16) made of bovine pericardium arranged at a proximal end (PE) thereof, a skirt (18) surrounding the dry valve (16) at the proximal end (PE) of the stent (10) and made of one of bovine pericardium and polyester, wherein the dry valve (16) is configured to be rehydrated when placed in contact with a solution, and the stent (10) comprising eyelets (22) arranged at the proximal end (PE) of the stent (10) for fixing the stent (10) at a point of interest, with the point of interest comprising one of the vena cava superior (SVC) and the vena cava inferior (IVC).

The self-expandable stent according to embodiment 2, which can include all features of embodiment 1, wherein the stent (10) comprises a distal end (DE) and a middle part (MP) arranged between the proximal end (PE) and the distal end (DE), and wherein the middle part (MP) is spaced approximately 20 to 40% from the distal end (DE) and approximately 20 to 40% from the proximal end (PE).

The self-expandable stent according to embodiment 3, which can include all features of embodiment 2, wherein the middle part (MP) extends over approximately 20 to 60% of a length of the stent (10).

The self-expandable stent according to embodiment 4, which can include all features of the preceding embodiments, wherein the stent (10) comprises a frame (12) composed of a plurality of arms (14) forming the three interconnected parts, i.e. the proximal end (PE), the distal end (DE) and the middle part (MP).

The self-expandable stent according to embodiment 5, which can include all features of embodiment 4, wherein, in the expanded state, the plurality of arms (14) is outwardly directed in the distal end (DE) of the frame (12).

The self-expandable stent according to embodiment 6, which can include all features of one of the preceding embodiments, wherein the frame (12) is composed of Nitinol.

The self-expandable stent according to embodiment 7, which can include all features of one of the preceding embodiments, wherein the stent (10) comprises a device or means (22) for attaching the proximal end (PE) of the stent (10) at the vena cava or at the transition between the vena cava and the right atrium of a heart.

The self-expandable stent according to embodiment 8, which can include all features of one of the preceding embodiments, wherein the dry bovine pericardium has a maximum tensile stress selected in the range of 15 to 25 MPa, and/or wherein the rehydrated bovine pericardium has a tensile stress selected in the range of 15 to 20 MPa.

The self-expandable stent according to embodiment 9, which can include all features of one of the preceding embodiments, wherein the dry bovine pericardium has a calcium content selected in the range of 0.01 to 0.1 g/Kg.

The self-expandable stent according to embodiment 10, which can include all features of one of the preceding embodiments, wherein the dry valve (16) comprises between two and six leaflets (20), The self-expandable stent according to embodiment 11, which can include all features of one of the preceding embodiments, wherein the dry valve (16) comprises four leaflets (20).

The self-expandable stent according to embodiment 12, which can include all features of one of the preceding embodiments, wherein the dry bovine pericardium is formed by treating using a method comprising the following steps:

(1) soaking of the bovine pericardium treated with a crosslinking agent with a saline solution;

(2) contacting the soaked bovine pericardium with an aqueous solution comprising Hydrogen Peroxide;

(3) contacting the bovine pericardium with an aqueous solution comprising PBS and EDTA;

(4) contacting the bovine pericardium with a solution comprising glycerol, ethanol and EDTA; and (5) contacting the bovine pericardium with a glycerol solution.

The self-expandable stent according to embodiment 13, which can include all features of one of the preceding embodiments, wherein the stent (10) is configured to be placed in the vena cava superior (SVC).

The self-expandable stent according to embodiment 14, which can include all features of embodiment 13, wherein, in the expanded state, a maximum outer diameter of the middle part (MP) is larger than a maximum outer diameter of the proximal end (PE).

The self-expandable stent according to embodiment 15, which can include all features of embodiment 14, wherein a transition between the middle part (MP) and the distal end (DE) has an outer diameter that is less than the maximum outer diameter of the middle part (MP) and less than an outer diameter of the distal end (DE) in the expanded state.

The self-expandable stent according to embodiment 16, which can include all features of one of embodiments 13 to 15, wherein the skirt (18) surrounds at least the proximal end (PE) and parts of the middle part (MP) of the stent (10).

The self-expandable stent according to embodiment 17, which can include all features of one of embodiments 13 to 16, wherein the skirt (18) surrounds up to ¾ of a length of the middle part (MP).

The self-expandable stent according to embodiment 18, which can include all features of embodiments 13 to 17, wherein, in the expanded state, the maximum outer diameter of the distal end (DE) and a maximum outer diameter of the proximal end (PE) are generally the same.

The self-expandable stent according to embodiment 19, which can include all features of embodiment 18, wherein a difference between the maximum outer diameter of the distal end (DE) and the maximum outer diameter of the proximal end (PE) lies in the range of 0 to 10%.

The self-expandable stent according to embodiment 20, which can include all features of one of embodiments 13 to 19, wherein all of the ends of the arms (14) at the distal end lie in a common plane and can comprise eyelets (22).

The self-expandable stent according to embodiment 21, which can include all features of one of embodiments 1 to 12, wherein the stent (10) is configured to be placed in the vena cava inferior (IVC).

The self-expandable stent according to embodiment 22, which can include all features of embodiment 21, wherein, in the expanded state, a maximum out the diameter of the stent (10) generally increases from the proximal end (PE) to the distal end (DE).

The self-expandable stent according to embodiment 23, which can include all features of embodiments 21 and 22, wherein the skirt (18) surrounds at least the proximal end (PE) of the stent (10).

The self-expandable stent according to embodiment 24, which can include all features of embodiments 21 to 23, wherein the skirt (18) surrounds up to ¼ of a length of the stent (10).

The self-expandable stent according to embodiment 25, which can include all features of one of the preceding embodiments 21 to 24, wherein all of the ends of the arms (14) at the distal end (DE) lie in a common plane and can comprise eyelets (22).

The invention further relates to a set of stents according to a first embodiment comprising two self-expendable stents, both stents (10*a*, 10*b*) having a dry valve (16) made of bovine pericardium arranged at a proximal end (PE) thereof, a skirt (18) surrounding the dry valve (16) at the proximal end (PE) of the stent (10) and made of one of bovine pericardium and polyester, wherein the dry valve (16) is configured to be rehydrated when placed in contact with a solution, and eyelets (22) arranged at the proximal end (PE) of the stent (10) for fixing the stent (10) at a point of interest such as the vena cava superior (SVC) or inferior (IVC), wherein a first stent (10*a*) is configured to be placed in the vena cava superior (SVC), in particular according to embodiments 1 to 20 and a second stent (10*b*) is configured to be placed in the vena cava inferior (IVC), in particular according to embodiments 1 to 12 and 21 to 25.

The invention further relates to a device according to a first embodiment for delivering a self-expandable stent according embodiments 1 to 25, the delivery device (30) comprising a flush port (32); a main body part (34) for holding, inflating and/or releasing the stent; and an actuation mechanism (38) for moving the stent (10) to a delivery site.

The device according to embodiment 2, which can include all features of embodiment 1, wherein the actuation mechanism (38) has a torque control and can rotate the stent (10) about an axis (B) of the main body (34).

The device according to embodiment 3, which can include all features of embodiments 1 and 2, with the device (30) having a knob (42) or the like at the actuation mechanism (38), with the knob (42) in particular being able to be rotated about an axis of rotation (B) of the actuation mechanism (38).

The invention further relates to a method of deploying a stent according to embodiments 1 to 20 and/or a set of stents according to embodiment 21 with a device for delivering said stent according to embodiments 22 to 24 for orthotopic and/or heterotopic applications at locations in the proximity of the tricuspid valve.

The method according to embodiment 2, which can include all features of embodiment 1 comprising at least the following steps:

providing at least one stent;

inserting said stent into a vein of a human or animal body using the delivery device;

moving said stent to an application site with said delivery device; and deploying said stent at the application site.

What is claimed:

1. A self-expandable stent comprising:

a dry valve made of dry bovine pericardium arranged at a proximal end of the stent; and a skirt surrounding the dry valve at the proximal end of the stent and made of one of dry bovine pericardium and polyester, the dry valve configured to be rehydrated when placed in contact with a solution, the stent comprising eyelets arranged at the proximal end of the stent to fix the stent at a point of interest, with the point of interest comprising one of a vena cava superior and a vena cava inferior, the dry bovine pericardium being formed by a method comprising:

soaking of the dry bovine pericardium treated with a crosslinking agent with a saline solution:

contacting the soaked bovine pericardium with an aqueous solution comprising hydrogen peroxide;

contacting the bovine pericardium with an aqueous solution comprising a phosphate buffered saline and ethylenediaminetetraacetic acid;

contacting the bovine pericardium with a solution comprising glycerol, ethanol and ethylenediaminetetraacetic acid; and contacting the bovine pericardium with a glycerol solution.

2. The self-expandable stent according to claim 1, further comprising a distal end and a middle part arranged between the proximal end and the distal end, and the middle part spaced approximately 20 to 40% from the distal end and approximately 20 to 40% from the proximal end.

3. The self-expandable stent according to claim 1, further comprising a frame including a plurality of arms forming three interconnected parts.

4. The self-expandable stent according to claim 3, wherein, in an expanded state, the plurality of arms is outwardly directed in a distal end of the frame.

5. The self-expandable stent according to claim 3, wherein the frame is composed of Nitinol.

6. The self-expandable stent according to claim 1, further comprising a device configured to attach the proximal end of the stent at the vena cava or at a transition between the vena cava and a right atrium of a heart.

7. The self-expandable stent according to claim 1, wherein the dry bovine pericardium has a maximum tensile stress selected in the range of 15 to 25 MPa, or the rehydrated bovine pericardium has a tensile stress selected in the range of 15 to 20 MPa.

8. The self-expandable stent according to claim 1, wherein the dry bovine pericardium has a calcium content selected in the range of 0.01 to 0.1 g/Kg.

9. The self-expandable stent according to claim 1, wherein the dry valve comprises between two and six leaflets.

10. The self-expandable stent according to claim 1, wherein the stent is configured to be placed in the vena cava superior.

11. The self-expandable stent according to claim 10, further comprising a distal end and a middle part arranged between the proximal end and the distal end, and in an expanded state, a maximum outer diameter of the middle part is larger than a maximum outer diameter of the proximal end.

12. The self-expandable stent according to claim 11, wherein a transition between the middle part and the distal end has an outer diameter that is less than the maximum outer diameter of the middle part and less than an outer diameter of the distal end in the expanded state.

13. The self-expandable stent according to claim 10, further comprising a distal end and a middle part arranged between the proximal end and the distal end, and the skirt surrounds at least the proximal end and parts of the middle part of the stent.

14. The self-expandable stent according to claim 10, further comprising a distal end and a middle part arranged between the proximal end and the distal end, and in an expanded state, the maximum outer diameter of the distal end and a maximum outer diameter of the proximal end are generally the same.

15. The self-expandable stent according to claim 10, further comprising a frame including a plurality of arms forming three interconnected parts, and a distal end, and the ends of the arms at the distal end lie in a common plane and comprise eyelets.

16. The self-expandable stent according to claim 1, wherein the stent is configured to be placed in the vena cava inferior.

17. The self-expandable stent according to claim 16, further comprising a distal end and a middle part arranged between the proximal end and the distal end, and in an expanded state, a maximum outer diameter of the stent generally increases from the proximal end to the distal end.

18. The self-expandable stent according to claim 16, wherein the skirt surrounds at least the proximal end of the stent.

19. The self-expandable stent according to claim 16, further comprising a frame including a plurality of arms forming three interconnected parts, and a distal end, and the ends of the arms at the distal end lie in a common plane and comprise eyelets.

20. A set of stents comprising:

two self-expandable stents, each of the two self-expandable stents having; a dry valve made of dry bovine pericardium arranged at a proximal end of the stent, and a skirt surrounding the dry valve at the proximal end of the stent and made of one of dry bovine pericardium and polyester, the dry valve configured to be rehydrated when placed in contact with a solution, and eyelets arranged at the proximal end of the stent to fix the stent at a point of interest such as a vena cava superior or inferior, a first stent of the two self-expandable stents configured to be placed in the vena cava superior, and a second stent of the two self-expandable stents configured to be placed in the vena cava inferior, the dry bovine pericardium of each of the two self-expandable stents being formed by a method comprising:

soaking of the dry bovine pericardium treated with a crosslinking agent with a saline solution;

contacting the soaked bovine pericardium with an aqueous solution comprising hydrogen peroxide;

contacting the bovine pericardium with an aqueous solution comprising a phosphate buffered saline and ethylenediaminetetraacetic acid;

contacting the bovine pericardium with a solution comprising glycerol, ethanol and ethylenediaminetetraacetic acid; and contacting the bovine pericardium with a glycerol solution.

* * * * *